United States Patent
Tang

(10) Patent No.: US 10,624,938 B2
(45) Date of Patent: Apr. 21, 2020

(54) **TOTAL FLAVONE EXTRACT OF FLOWER OF *ABELMOSCHUS MANIHOT* L. MEDIC AND PREPARATION METHOD THEREOF**

(76) Inventor: Renmao Tang, Jiangyan (CN)

( * ) Notice: Subject to any disclaimer, the term of this patent is extended or adjusted under 35 U.S.C. 154(b) by 0 days.

(21) Appl. No.: 14/386,781

(22) PCT Filed: Sep. 4, 2012

(86) PCT No.: PCT/CN2012/080972
§ 371 (c)(1),
(2), (4) Date: Sep. 19, 2014

(87) PCT Pub. No.: WO2013/139111
PCT Pub. Date: Sep. 26, 2013

(65) Prior Publication Data
US 2015/0050375 A1    Feb. 19, 2015

(30) Foreign Application Priority Data

Mar. 21, 2012 (CN) .......................... 2012 1 0082553

(51) Int. Cl.
*A61K 36/185* (2006.01)
*A61K 31/352* (2006.01)
*A61K 31/7034* (2006.01)

(52) U.S. Cl.
CPC .......... *A61K 36/185* (2013.01); *A61K 31/352* (2013.01); *A61K 31/7034* (2013.01); *A61K 2236/00* (2013.01)

(58) Field of Classification Search
None
See application file for complete search history.

(56) References Cited

FOREIGN PATENT DOCUMENTS

| CN | 1615947 A | 5/2005 |
|---|---|---|
| CN | 200610097615 | 11/2006 |
| CN | 1994337 A | 7/2007 |
| CN | 200410035741 | 7/2008 |
| CN | 101385748 A | 3/2009 |
| CN | 102319275 A | 1/2012 |
| CN | 102600219 A | 7/2012 |

OTHER PUBLICATIONS

An et al. (2011) Fitoterapia 82, 595-600.*
Cheng et al. (2006) Neuroscience Research 55, 142-145.*
International Search Report for PCT/CN2012/080972 dated Dec. 13, 2012.
Written Opinion for PCT/CN2012/080972 dated Dec. 13, 2012.
Lu Linling, A quantitative method using one marker for simultaneous assay of seven flavonoids in the flowers of Abelmoschus manihot, Journal of Pharmaceutical Analysis, Dec. 31, 2013, p. 2082-2087, vol. (issue): 12 (33).

* cited by examiner

*Primary Examiner* — Terry A McKelvey
*Assistant Examiner* — Russell G Fiebig
(74) *Attorney, Agent, or Firm* — Bayramoglu Law Offices LLC

(57) ABSTRACT

Disclosed are a total flavone extract of *Abelmoschus Manihot* and preparation method thereof. The weight ratio of gossypetin-3'-glucoside, quercetin-3'-glucoside and isoquercetin in the extract is (11-16):(2.5-6):(4-6.5).

2 Claims, No Drawings

TOTAL FLAVONE EXTRACT OF FLOWER OF *ABELMOSCHUS MANIHOT* L. MEDIC AND PREPARATION METHOD THEREOF

CROSS REFERENCE TO RELATED APPLICATIONS

The present application is the U.S. National Stage of International Patent Application PCT/CN2012/080972 filed on Sep. 4, 2012, which claims the priority of Chinese patent application No. 201210082553.7 filed with the Chinese Patent Office on 21 Mar. 2012, entitled "total flavone extract of flower of *Abelmoschus Manihot* L. *Medic* and preparation method thereof", which are incorporated into the present application by reference in their entireties.

TECHNICAL FIELD

The technology of the present invention belongs to the pharmaceutical field of traditional Chinese medicine, in particular to an extract of flower of *Abelmoschus Manihot* (L.) *Medic*, formulation thereof and method for preparing the same, the extract of flower of *Abelmoschus Manihot* (L.) *Medic* can be used for pharmaceuticals, health care products and foods.

BACKGROUND

Flower of *Abelmoschus Manihot* (L.) *Medic* is the dried flower of *Abelmoschus Manihot* (L.) *Medic* belonging to plants of *Abelmoschus* of malvaceae, the *Abelmoschus Manihot* (L.) *Medic* was first recorded in the "Jiayou Materia Medica", it is widely distributed with abundant resources. It is recorded in the "Compendium of Materia Medica" that, the flower of *Abelmoschus Manihot* (L.) *Medic*, which is sweet in smell, cold and slippery in nature and non-toxic, is mainly used for treating dribbling urination and hastening parturition, enables the patients suffering from malignant sore pus and having not being cured for a long time to recover from illness after applying its powder, and is an effective drug for treating illness of sores, and used for reducing carbuncle swelling and treating scald due to immersion in oil and boiling water and fire burns, etc. According to modern medicine, the main active ingredients of flower of *Abelmoschus Manihot* (L.) *Medic* are ingredients of flavones, current research on the chemical components is also concentrated in the total flavone of flower of *Abelmoschus Manihot* (L.) *Medic* (TFA) and monomer thereof. Seven monomers of flavones have been isolated and identified since 1980s. Studies demonstrate that the isolated monomers can reduce proteinuria and red blood cells in urine, alleviate tubulointerstitial lesions, eliminate oxygen free radicals, increase immune adhesion of red blood cells, promote transportation and removal of human circulating immune complexes (CIC), regulate immune function of cells and inhibit the degree of humoral immune response, thereby alleviating CIC-mediated renal injury and improving the function of kidney, so that the purpose of treating chronic kidney disease (CKD) can be achieved.

Pharmacological studies show that compounds of flavones are the main bioactive ingredients in flower of *Abelmoschus Manihot* (L.) *Medic*. Further chemical studies show that, the following nine compounds are in high contents in the compounds of flavones (or referred to as total flavone) in flower of *Abelmoschus Manihot* (L.) *Medic*: hyperin, isoquercetin, quercetin-3'-glucoside, gossypetin-3'-glucoside, myricetin-3-glucoside, quercetin-3-robinobioside, gossypetin, myricetin and quercetin, the formula of the nine compounds are as follows:

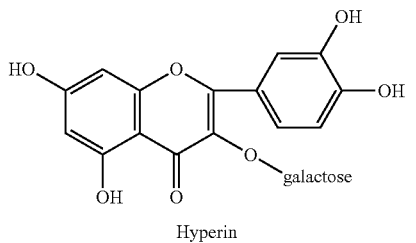

Hyperin

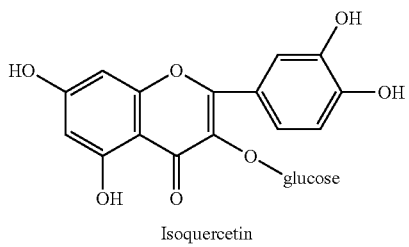

Isoquercetin

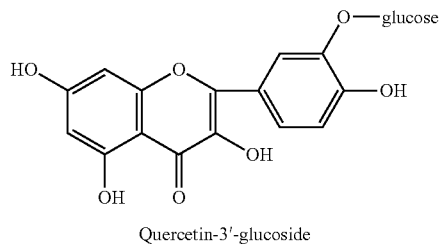

Quercetin-3'-glucoside

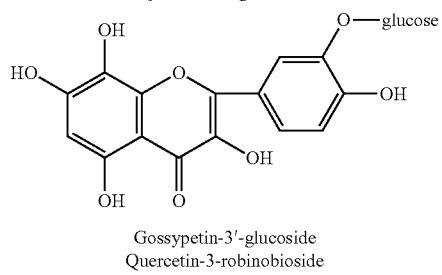

Gossypetin-3'-glucoside
Quercetin-3-robinobioside

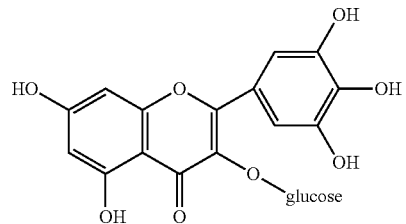

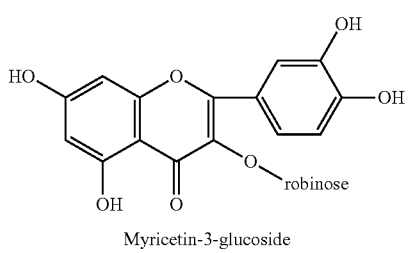

Myricetin-3-glucoside

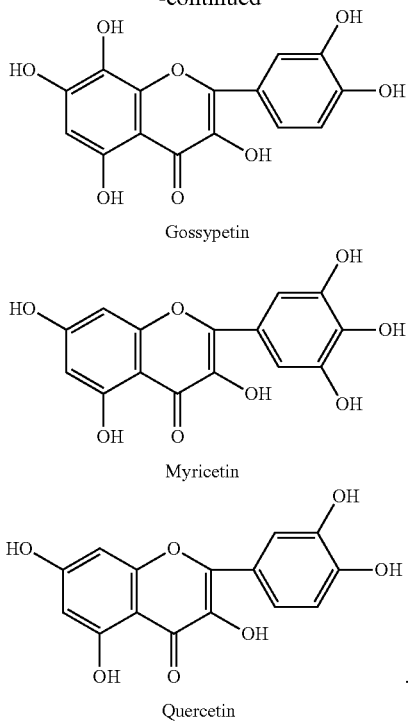

Gossypetin

Myricetin

Quercetin

Current methods for preparing the total flavone extract of flower of *Abelmoschus Manihot* (L.) *Medic* can be summarized into the following three methods.

1. Extraction is performed with water or alcohol first, and the extract after recovering of the solvent is suspended in water, then extraction is performed with chloroform, ethyl acetate and n-butanol respectively, and the resulting extract is divided into several parts, and then chromatography and isolation is performed with a silica gel column or Sephadex column to obtain a single component material.

2. Extraction is performed with ethanol, the extracts are combined and filtered and the filtrate is concentrated, then the concentrated liquid is diluted with an appropriate amount of water, and gradient elution is performed with the alcohol aqueous solution through a macroporous resin column or polyamide column, then the eluate is concentrated, dried and pulverized to obtain the total flavone extract, this method can refer to the method for preparing the total flavone extract of flower of *Abelmoschus Manihot* (L.) *Medic* disclosed in the patent application for invention with application No. 200410035741.X.

3. Extraction is performed with ethanol and the extracts are combined, the extract is concentrated under reduced pressure to become an extractum having the specific gravity of 1.13-1.16 at 60° C., and the extractum is added with boiling water several times to be dissolved, and let to stand and filtered, and chromatography is performed on the filtrate by a macroporous adsorption resin column or polyamide column, then the column is eluted with methanol and the eluate is collected; the eluate is concentrated under reduced pressure and dried in vacuum to obtain the crude total flavone extract of flower of *Abelmoschus Manihot* (L.) *Medic*; then the crude total flavone extract is refined and extracted with ethyl acetate-ethanol, and the solvent is recovered from the extract, then the extract is dried under reduced pressure or in vacuum to obtain the total flavone extract of flower of *Abelmoschus Manihot* (L.) *Medic*, this method can refer to the method for preparing the total flavone extract of flower of *Abelmoschus Manihot* (L.) *Medic* disclosed in the patent application for invention with application No. 200610097615.6.

The kind and content of compounds of flavones contained in the extract extracted by different methods are different, in other words, different compositions and weight ratios of total flavones lead to different pharmacological activity and great difference in potency, which means that the substance extracted by each extraction method is a new substance (composition). Although it is deemed that compounds of flavones are active ingredients currently, it has not been determined in the prior art that which compound(s) in these compounds of flavones is(are) the main active ingredient(s), the present invention determines the main compounds of flavones by a large number of experiments. The present invention further optimizes the weight ratio among the main active ingredients, for the contents of flavones in the current total flavone extract of flower of *Abelmoschus Manihot* (L.) *Medic*, gossypetin-3'-glucoside<quercetin-3'-glucoside≤isoquercetin, and the content of gossypetin-3'-glucoside is usually half of that of isoquercetin or quercetin-3'-glucoside, in the total flavone extract of flower of *Abelmoschus Manihot* (L.) *Medic* in the present invention, the content of gossypetin-3'-glucoside is basically over 2 times that of isoquercetin or quercetin-3'-glucoside, meanwhile, the extract of the present invention also has better effects in the treatment of kidney diseases.

In view of the above, there is urgent need to provide a total flavone extract of flower of *Abelmoschus Manihot* (L.) *Medic* with definite effective ingredients, better efficacy and stability, safety and reliability, reasonable and feasible process, and stable quality, and preparation method thereof, which is suitable for the large-scale production of enterprises, solving the problem that the flower of *Abelmoschus Manihot* (L.) *Medic* formulation is taken in high dose to provide convenience and benefits for patients.

SUMMARY

The present invention aims to provide a total flavone extract of flower of *Abelmoschus Manihot* (L.) *Medic*, with definite and complete active ingredients, more stable quality, better efficacy and stability, safety and reliability, simple preparation process and low cost, which is suitable for industrial large-scale production, formulation and preparation method thereof; by the method for preparing a total flavone extract of flower of *Abelmoschus Manihot* (L.) *Medic*, the problem of low content and quality of active ingredients in the total flavone extract of flower of *Abelmoschus Manihot* (L.) *Medic* is solved, especially, the preparation method of the present invention is suitable for industrial large-scale production, and can be operated simply and is easy to control, by applying the preparation method of the present invention in the industrial production, the active ingredients in the total flavone extract of flower of *Abelmoschus Manihot* (L.) *Medic* has more optimal proportions, high content and quality, solving the problem that the flower of *Abelmoschus Manihot* (L.) *Medic* is taken in high dose.

To implement the present invention, the present invention provides the following technical solutions.

A total flavone extract of flower of *Abelmoschus Manihot* (L.) *Medic*, comprising gossypetin-3'-glucoside, quercetin-3'-glucoside and isoquercetin, wherein the weight ratio of gossypetin-3'-glucoside, quercetin-3'-glucoside and isoquercetin is (11-16):(2.5-6):(4-6.5).

Preferably, the weight ratio of gossypetin-3'-glucoside, quercetin-3'-glucoside and isoquercetin may be (12-15):(3-5):(4-6), (13-14):(4-5):(4-5), (11-16):(4-5):(4-5), (12-15):(2.5-6):(4-6.5) or (12-15):(4-5):(4-6.5).

Preferably, based on the total weight of the extract, the content of total flavone in the extract by weight percentage is greater than 50%.

Preferably, the extract further contains quercetin and quercetin-3-robinobioside; the extract further contains hyperin and gossypetin; the extract further contains myricetin and myricetin-3-glucoside.

The present invention further provides a pharmaceutical composition, comprising the total flavone extract of flower of *Abelmoschus Manihot* (L.) *Medic* and a pharmaceutically acceptable carrier.

The pharmaceutically acceptable carrier comprises or may be various excipients, lubricants, binders, disintegrating agents, stabilizers, foaming agents and coating agents, etc, which are used for solid formulations; or solvents, solubilizers, suspending agents, isotonic agents, buffering agents, emollients and emulsifiers, etc, which are used for semi-solid formulations and liquid formulations; in addition, other pharmaceutically acceptable additives such as preservatives, antioxidants, coloring agents, sweetening agents and flavoring agents may be used as required.

Specifically, examples of the pharmaceutically acceptable carrier include, but are not limited to, one or more of starch, dextrin, lactose, microcrystalline cellulose, hydroxypropylmethyl cellulose, polyethylene glycol, magnesium stearate, talc powder, calcium sulfate, micronization silica gel, xylitol, lactitol, glucose, glycine, mannitol and hydroxypropyl-β-cyclodextrin, etc.

Preferably, the pharmaceutical composition is capsule, tablet, injection, solution, syrup, granule, pill, powder, paste, patch, soft capsule, hard capsule or dropping pill.

The technical solutions of the present invention also include use of the total flavone extract of flower of *Abelmoschus Manihot* (L.) *Medic* in the preparation of a medicament for treating kidney diseases.

The technical solutions of the present invention also include use of the total flavone extract of flower of *Abelmoschus Manihot* (L.) *Medic* in the preparation of foods, beverages and health care products. The total flavone extract of flower of *Abelmoschus Manihot* (L.) *Medic* can be made into foods, beverages and health care products in various forms (such as liquid, solid and powder) by adding an ordinary additive as a component.

The total flavone extract of flower of *Abelmoschus Manihot* (L.) *Medic* can be prepared according to the following methods:

1. The flower of *Abelmoschus Manihot* (L.) *Medic* is extracted with 6-18 times amount (i.e, the ratio of liquid to solid is 6-18 ml/g) of 40-95% ethanol solution 1-3 times for 1-4 hours each time, ethanol is recovered from alcohol extract and then the extract is concentrated to a relative density of 1.10-1.35 to obtain the concentrated liquid, and the weight ratio of gossypetin-3'-glucoside, quercetin-3'-glucoside and isoquercetin is adjusted to (11-16):(2.5-6):(4-6.5) by adding a monomer compound of gossypetin-3'-glucoside, quercetin-3'-glucoside or isoquercetin into the concentrated liquid according to the contents of the three compounds in the concentrated liquid to obtain the total flavone extract of flower of *Abelmoschus Manihot* (L.) *Medic* of the present invention.

Wherein the monomer of gossypetin-3'-glucoside, quercetin-3'-glucoside or isoquercetin can be prepared according to the prior art, such as the method mentioned in the section of "Extraction and Isolation" of "Studies on the Flavonol Constituents of *Abelmoschus Manihot* L. *Medic*" (Xianrong Wang, Zhenghua Zhou et al, "Chinese Journal of Natural Medicines", Vol. 2, No. 2, Pages 91-93, March 2004).

Preferably, in the alcohol extraction process of the method, extraction is performed by adding 12 times amount of 60% ethanol solution twice for 2 hours each time to make the relative density of the concentrated liquid reach 1.15; or extraction is performed by adding 10 times amount of 80% ethanol solution twice for 1.5 hours each time to make the relative density of the concentrated liquid reach 1.20; or extraction is performed by adding 8 times amount of 90% ethanol solution twice for 1 hour each time to make the relative density of the concentrated liquid reach 1.18.

2. The flower of *Abelmoschus Manihot* (L.) *Medic* is extracted with 6-18 times amount (i.e, the ratio of liquid to solid is 6-18 ml/g) of 40-95% ethanol solution 1-3 times for 1-4 hours each time, ethanol is recovered from alcohol extract and then the extract is concentrated to a relative density of 1.10-1.35 to obtain concentrated liquid, then the concentrated liquid is passed through a silica gel column, and gradient elution is performed with chloroform-methanol, different eluates are selected and mixed to make the weight ratio of gossypetin-3'-glucoside, quercetin-3'-glucoside and isoquercetin reach (11-16):(2.5-6):(4-6.5) according to the contents of the three compounds in respective eluates, the eluates are collected, concentrated, dried and pulverized to obtain the total flavone extract of flower of *Abelmoschus Manihot* (L.) *Medic* of the present invention. Gradient elution may be performed with chloroform-methanol at a volume ratio of 20:80, 30:70, 40:60, 50:50, 60:40, 70:30 and 80:20 sequentially, and the eluates obtained by eluting with chloroform-methanol at a volume ratio of (30:70), (50:50) and (80:20) are collected. Gradient elution may also be performed with chloroform-methanol at a volume ratio of 10:90, 25:75, 44:66, 55:45, 67:33 and 85:15 sequentially, and the eluates obtained by eluting with chloroform-methanol at a volume ratio of (25:75) and (67:33) are collected. Different eluates are selected and mixed to make the weight ratio of gossypetin-3'-glucoside, quercetin-3'-glucoside and isoquercetin reach (11-16):(2.5-6):(4-6.5) according to the contents of the three compounds in respective eluates.

Preferably, in the alcohol extraction process of the method, extraction is performed by adding 12 times amount of 60% ethanol solution twice for 2 hours each time to make the relative density of the concentrated liquid reach 1.15; or extraction is performed by adding 10 times amount of 80% ethanol solution twice for 1.5 hours each time to make the relative density of the concentrated liquid reach 1.20; or extraction is performed by adding 8 times amount of 90% ethanol solution twice for 1 hour each time to make the relative density of the concentrated liquid reach 1.18.

3. The flower of *Abelmoschus Manihot* (L.) *Medic* is extracted with 6-18 times amount (i.e, the ratio of liquid to solid is 6-18 ml/g) of 40-95% ethanol solution 1-3 times for 1-4 hours each time, and ethanol is recovered from alcohol extract and then the extract is concentrated to a relative density of 1.10-1.35 to obtain concentrated liquid, the concentrated liquid is passed through macroporous adsorption resin or polyamide resin, and elution is performed first with 1-5 column volumes of water, then with 1-4 column volumes of 10-20% ethanol or methanol solution, and then with 1-4 column volumes of 60-80% ethanol or methanol solution, the eluate obtained by eluting with 60-80% ethanol or methanol solution is collected, concentrated and dried to obtain a crude extract, gradient extraction is performed on the crude extract with ethyl acetate-ethanol mixture or ethyl acetate-methanol mixture at different proportions sequentially, and part of the extract are combined and then concentrated and dried. Gradient extraction is performed with ethyl acetate-ethanol mixture or ethyl acetate-methanol mixture at a volume ratio of 18:82, 38:62, 52:48 and 68:32 sequentially, and the extracts obtained by extracting with mixture at a volume ratio of (18:82) and (68:32) are combined. Gradient extraction can also be performed with the mixture at different volume ratios, different extracts are selected and mixed to make the weight ratio of gossypetin-3'-glucoside, quercetin-3'-glucoside and isoquercetin reach (11-16):(2.5-6):(4-6.5) according to the contents of the three compounds in respective extracts.

Preferably, in the alcohol extraction process of the method, extraction is performed by adding 12 times amount of 60% ethanol solution twice for 2 hours each time to make the relative density of the concentrated liquid reach 1.15; or extraction is performed by adding 10 times amount of 80% ethanol solution twice for 1.5 hours each time to make the relative density of the concentrated liquid reach 1.20; or extraction is performed by adding 8 times amount of 90% ethanol solution twice for 1 hour each time to make the relative density of the concentrated liquid reach 1.18.

Preferably, in the elution process by the macroporous adsorption resin column or polyamide resin column, the concentrated liquid is adsorbed at a speed of 1-3 BV/h (column volumes/hour), and elution is performed with 3 column volumes of water at a speed of 1 BV/h, then performed with 3 column volumes of 15% ethanol solution at a speed of 1 BV/h, and then performed with 4 column volumes of 70% ethanol solution at a speed of 1 BV/h, then the eluate obtained by eluting with 70% ethanol or methanol solution is collected.

For the contents of flavones in the existing total flavone extract of flower of *Abelmoschus Manihot* (L.) *Medic*, gossypetin-3'-glucoside<quercetin-3'-glucoside≤isoquercetin, and the content of gossypetin-3'-glucoside is usually half of that of isoquercetin or quercetin-3'-glucoside, the present invention further optimizes the weight ratio among the main active ingredients, in the total flavone extract of flower of *Abelmoschus Manihot* (L.) *Medic* of the present invention, the content of gossypetin-3'-glucoside is basically over 2 times that of isoquercetin or quercetin-3'-glucoside, in addition, compared to the existing total flavone extract of flower of *Abelmoschus Manihot* (L.) *Medic*, the total flavone extract of flower of *Abelmoschus Manihot* (L.) *Medic* of the present invention also gets better effects on treatment of kidney diseases.

The beneficial effects of the total flavone extract of flower of *Abelmoschus Manihot* (L.) *Medic* and its preferred formulations are further illustrated by the following test examples.

Experiment of treating rat kidney disease model in each group by the total flavone extract of flower of *Abelmoschus Manihot* (L.) *Medic* of the present invention Experimental animals and grouping: 40 male SD white rats of healthy adult (5 weeks old), weighing 150±25 g per rat (provided by Laboratory Animal Center in Jiangsu Province) were taken. The rats were fed adaptively for 7 days, and randomly divided into 5 groups with 8 rats in each group based on the weight of rats. In addition to the blank control group, puromycin-induced rat nephropathy models were established in the remaining four groups according to the following methods. The animal model is prepared as follows: at the first day after grouping of rats, rats were injected intraperitoneally once with puromycin amino nucleoside (PAN) at 100 mg/kg body weight.

1) Blank control group: no medicine was taken by rats, and models were not established.

2) Pathological model group: puromycin-induced rat nephropathy model was prepared according to the above method.

3) Control group: starting from establishment of the model, rats were administrated intragastrically once daily with powder of flower of *Abelmoschus Manihot* (L.) *Medic* extract prepared according to Example 1 of patent application CN200610097615.6 (equivalent to 8.4 g/kg·d raw herbs) for two consecutive weeks.

4) Test Group 1: starting from establishment of the model, rats were administrated intragastrically once daily with powder of flower of *Abelmoschus Manihot* (L.) *Medic* extract prepared according to Example 1 of the present invention (equivalent to 8.4 g/kg·d raw herbs) for two consecutive weeks.

5) Test Group 2: starting from establishment of the model, rats were administrated intragastrically once daily with powder of flower of *Abelmoschus Manihot* (L.) *Medic* extract prepared according to Example 2 of the present invention (equivalent to 8.4 g/kg·d raw herbs) for two consecutive weeks.

Before establishment of models, and at $7^{th}$, $12^{th}$ and $16^{th}$ days during establishment of models, urine protein of each rat was measured. The experimental results are shown in the table below.

TABLE 1

| | Quantitative changes of urine protein for each group (mg/24 hr mean ± SD) | | | |
|---|---|---|---|---|
| Group | Before establishment of model | $7^{th}$ day | $12^{th}$ day | $16^{th}$ day |
| Blank control group | 2.9 ± 1.8 | 3.4 ± 2.1 | 3.2 ± 1.3 | 2.6 ± 1.4 |
| Pathological model group | 2.5 ± 1.3 | 335.3 ± 62.6 | 412.1 ± 104.5 | 386.3 ± 92.7 |
| Positive control group | 2.7 ± 1.9 | 262.65 ± 81.9## | 241.6 ± 72.24## | 218.7 ± 63.8## |
| Test group 1 | 2.8 ± 2.4 | 201.0 ± 65.4*## | 187.7 ± 53.6*## | 165.3 ± 52.5*## |
| Test group 2 | 3.0 ± 2.3 | 180.4 ± 62.6## | 172.1 ± 52.7## | 154.4 ± 41.8**## | represents P < 0.01 compared with the pathological model group;
*represents P < 0.05 compared with the positive control group;
**represents P < 0.01 compared with the positive control group.

Conclusion: The above tests show that the extract of flower of *Abelmoschus Manihot* (L.) *Medic* prepared by the present invention can significantly reduce the amount of urine protein of puromycin-induced nephropathy in rats, indicating that the pharmacological activity of the extract of flower of *Abelmoschus Manihot* (L.) *Medic* prepared by the present invention is higher than that of the total flavone of flower of *Abelmoschus Manihot* (L.) *Medic* produced according to the existing technology.

Conditions for clinical observation of the medicine of the present invention:

1. General Information

A total of 242 outpatients were treated, with 128 males and 114 females. 30 outpatients are aged 18-30 years old, 32 outpatients are aged 31-40 years old, 44 outpatients are aged 41-50 years old, and 16 outpatients are aged 51-70 years old.

2. Diagnostic Criteria (1) Diagnostic Criteria of Traditional Chinese Medicine Damp-Heat Syndrome of Chronic Nephritis Main Symptoms:
1) edema of face or limb.
2) distending pain of lumbus, heat pain, percussion pain.
3) recurrent sore throat, swelling tonsillitis or flu-induced exacerbations.
4) furuncle of skin, sores, etc. or skin infection-induced exacerbations.
5) urine being dark yellow and turbid, having more foam, hematuria, burning sensation during urination, difficulty and pain in urination, or urinary tract infection-induced exacerbations.
6) yellow and greasy tongue coating, or yellow and greasy tongue root, red tongue.
7) number of pyocytes in urine is more than 5/HP, or urinary sediment count WBC is more than 400,000/hr.

Secondary Symptoms:
1) bitter taste in mouth, halitosis, sticky sensation in mouth or dry mouth;
2) stuffy feeling in chest, abdominal distension, anorexia;
3) nausea and vomiting;
4) grimy sloppy stool, difficulty in defecation with uncomfortable feeling, or dry or closed stool;
5) pulse moisten or slippery;
6) urine sialic acid (USA)>90 mg/L;
7) urinary N-acetyl-β-glucosaminidase $(U_{NAG})>25^{U}/L$.

Anyone who shows the symptoms of item 1) in main symptoms and above 1 item in secondary symptoms; or shows the symptom of above 2 items in main symptoms; or shows the symptom of over 3 items in secondary symptoms can be diagnosed as this disease.

(2) Diagnostic Criteria of Western Medicine

Chronic Nephritis
1) slow onset, refractory protracted illness, frequently occurring with varying degrees, gradually declining of renal function in the later stage, anemia, disorder of electrolyte, increasing of blood BUN and Cr, etc;
2) showing different degrees of proteinuria, hematuria, edema and hypertension in varying levels;
3) acute exacerbation being induced due to respiratory infection in the course and other reasons, there being symptoms similar to that of acute kidney disease.

(3) Severity Grading Standard of Chronic Kidney Disease

The severity of disease is judged mainly from proteinuria, renal function, edema, hypertension and other aspects, which can be determined if there is any one of the following items.

Mild: 1) qualitative test for urine protein continuously shows +~++, or quantitative test for urine protein continuously shows no more than 1 g/day, and renal function is normal; 2) edema is not obvious, and blood pressure is normal.

Moderate: 1) qualitative test for urine protein continuously shows ++~+++, or quantitative test for urine protein continuously shows 1~2 g/day, and renal function is normal; 2) edema may be mild or severe, and there may be high blood pressure.

Severe: 1) qualitative test for urine protein continuously shows +++~++++, or quantitative test for urine protein continuously shows 2.1~3.5 g/day (serum albumin>30 g/L); 2) renal function is abnormal; 3) there is obvious edema and hypertension.

(4) Method for Treatment

Capsules in the test group (capsules prepared according to Example 4 of the present invention): three times a day with 3 capsules per time.

Capsules in the control group (capsules prepared according to Example 8 of Patent application CN200610097615.6): orally, three times a day with 3 capsules per time.

Capsules are taken continuously for 8 weeks. Patients in complete or basic remission are continuously treated for follow-up 12 weeks. Patients with hypertension and diabetes are combined, and it is permitted to take the antihypertensive drugs previously taken.

(5) Evaluation Criteria of Efficacy 1) classification of efficacy complete remission: symptoms such as edema and physical signs disappear completely, and test for urine protein continuously shows negative or "±", or 24-hour urine protein quantification test continuously shows that the amount of urine protein is less than 0.2 g, red blood cells in urine disappear at high magnification, and the renal function is normal.

basic remission: symptoms such as edema and physical signs disappear basically, and test for urine protein continuously shows that the amount of urine protein decreases by above 50%, number of red blood cells in urine is no less than 3~5 at high magnification, and the renal function is normal or basically normal (with difference no less than 15% relative to normal).

Improved: symptoms such as edema and physical signs are significantly improved, and test for urine protein continuously shows that urine protein decreases by one +, or 24-hour urine protein quantification test continuously shows that the amount of urine protein decreases by 25~49%, number of red blood cells in urine is no less than 5~8 at high magnification, and the renal function is normal or improved.

Invalid: clinical manifestations and symptoms of laboratory tests described above were not improved significantly or aggravated.

2) Cannot be evaluated: efficacy cannot be accurately evaluated due to compliance of patients and other subjective and objective reasons.

3) Comparing changes of the main outcome measures among groups and that between pre-treatment and post-treatment.

(6) Analysis of Efficacy

TABLE 12

Efficacy observation after a course of treatment

|  | Cases | Comprehensive efficacy | | | | |
| --- | --- | --- | --- | --- | --- | --- |
|  |  | Complete remission ratio (%) | Basic remission ratio (%) | Improved (%) | Invalid (%) | Total effective rate (%) |
| Test group | 80 | 26/80 | 43/80 | 5/80 | 6/80 | 92.5 |
| Control group | 80 | 15/80 | 40/80 | 4/80 | 21/80 | 73.7 |
| Efficacy comparison between two groups |  | P < 0.01 | | | | |

The results listed in the above table show that the test group is better than the control group, the flower of *Abelmoschus Manihot* (L.) *Medic* formulation of the present invention has good efficacy.

The contents of the total flavone extract of flower of *Abelmoschus Manihot* (L.) *Medic* and formulations thereof were measured according to the following method:

The measurement was performed according to the high performance liquid chromatography (Chinese Pharmacopoeia 2005 edition Volume 1 appendix VI D).

Chromatographic conditions and system suitability test: filler: octadecylsilane; detection wavelength: 360 nm; column temperature: room temperature; mobile phase: acetonitrile (A)-2% acetic acid (B); gradient: 0 min: A-16%, B-84%, 20 min: A-16%, B-84%, 30 min: A-20%, B-80%, 40 min: A-16%, B-84%.

Number of theoretical plates which is calculated based on each main peak shall not be less than 5000. Degree of separation between hyperin and isoquercetin is greater than 1.5, and degree of separation between quercetin-3'-glucoside and gossypetin-3'-glucoside is good. Preparation of the control solution: an appropriate amount of hyperin reference substance, isoquercetin reference substance and quercetin-3'-glucoside reference substance were taken respectively, and added with methanol to prepare 100 μg/ml, 40 μg/ml and 40 μg/ml solution respectively; in addition, an appropriate amount of gossypetin-3'-glucoside reference substance was taken, and added with mobile phase to prepare a solution of 80 μg/ml.

Preparation of the test solution: contents within load difference of the product were taken and ground into fine powder, 0.1 g fine powder was taken, and precisely weighed and put into 25 ml volumetric flask, then about 15 ml methanol was added into the volumetric flask, and ultrasonic treatment was performed for 30 minutes (frequency of 40 KHz, power of 100 W and power supply of 220V). Then the solution was let to cool, methanol was added into the flask mark to make the diluted solution reach scale of the volumetric flask, the solution was shaken up and filtrated with a microporous filtration membrane, and the filtrate was taken, so that the test solution was obtained.

Method for determination: 10 μl test solution and 10 μl control solution were precisely drawn respectively, and injected into the liquid chromatography to perform measurement, and calculation was performed according to the external standard method.

Content of total flavone was determined by the $AlCl_3$ complexation colorimetry method, and the results show that this product contains 50-90% total flavone (calculated based on rutin).

Qualitative analysis is performed on quercetin, quercetin-3-robinobioside, gossypetin, myricetin and myricetin-3-glucoside in the extract of the present invention by using LC-MS chromatography, LC-MS chromatographic conditions: 1. liquid chromatographic conditions: chromatographic column: Hypersil ODS C18 column (150 mm×4.6 mm, 5 μm); detection wavelength: 358 nm; mobile phase: methanol-water-glacial acetic acid (60:40:0.5), flow rate: 0.5 mL/min, column temperature: room temperature, injection volume: 50 μL. 2. Mass spectra (MS) conditions Electrospray ionization (ESI) ion source with ejection voltage of 4500 eV; atomizing gas (N2) with a pressure of 50 psi and a flow rate of 50 flow units (a.u.); drying gas (N2) with a flow rate of 10 a.u.; positive and negative ionization full scan mode. The obtained results were compared with the existing MS data.

DETAILED DESCRIPTION OF THE EMBODIMENTS

Methods for preparing the total flavone extract of flower of *Abelmoschus Manihot* (L.) *Medic* and formulations thereof in the present invention will be further illustrated through examples hereinafter.

Specific Examples

Flower of *Abelmoschus Manihot* (L.) *Medic* is the dried flower of *Abelmoschus Manihot* (L.) *Medic* belonging to plants of *Abelmoschus* of malvaceae.

Raw materials of flower of *Abelmoschus Manihot* (L.) *Medic* are provided by *Abelmoschus Manihot* (L.) *Medic* GAP cultivation base of SZYY Group Pharmaceutical Ltd in Jiangsu province, other raw materials are all commercially available, and the raw materials are in accordance with the standards in the items of "Flower of *Abelmoschus Manihot* (L.) *Medic*" of PRC (People's Republic of China) Pharmacopoeia 2010 edition Volume 1.

Example 1

Preparation of the Total Flavone Extract of Flower of *Abelmoschus Manihot* (L.) *Medic*

The raw herbal material of flower of *Abelmoschus Manihot* (L.) *Medic* of the present invention is in an amount of 2000 g.

Reflux extraction was performed on flower of *Abelmoschus Manihot* (L.) *Medic* by 8 times amount of 95% ethanol solution twice for 1 hour each time, and filtration was performed, then the filtrates were combined and ethanol was recovered until there was no ethanol in the filtrate, and the filtrate was concentrated to a specific gravity of 1.20, then the concentrated liquid is made to stand at 0~4° C. for 24~48 hours, and the pH of the liquid is adjusted to 6.0, and the refrigerated liquid was dried fast by thin layer to obtain the crude extract of flower of *Abelmoschus Manihot* (L.) *Medic*.

The content of the total flavone in the above extract reaches 55.0% by weight percentage, wherein the total flavone extract contains the following ingredients: 1.20% hyperin, 1.50% isoquercetin, 1.00% quercetin-3'-glucoside and 0.9% gossypetin-3'-glucoside. An appreciate amount of the crude extract was taken, and added with quercetin-3'-glucoside and gossypetin-3'-glucoside to adjust the weight ratio of gossypetin-3'-glucoside, quercetin-3'-glucoside and isoquercetin to 16:4:4, it was identified by LC-MS chromatography that the extract still contains quercetin, quercetin-3-robinobioside, gossypetin, myricetin and myricetin-3-glucoside.

Example 2

Preparation of the Total Flavone Extract of Flower of *Abelmoschus Manihot* (L.) *Medic*

The raw herbal material of flower of *Abelmoschus Manihot* (L.) *Medic* of the present invention is in an amount of 1000 g.

Reflux extraction was performed on flower of *Abelmoschus Manihot* (L.) *Medic* by 10 times amount of 85% ethanol solution 3 times for 2 hours each time, and filtration was performed, then the filtrates were combined and ethanol was recovered until there was no ethanol in the filtrate, and the filtrate was concentrated to a specific gravity of 1.35, then the concentrated liquid was passed through a silica gel column, gradient elution was performed with chloroform-methanol, and the eluate was collected, concentrated, dried and pulverized to obtain the total flavone extract of flower of *Abelmoschus Manihot* (L.) *Medic*. Gradient elution was performed with 3 column volumes of chloroform-methanol at a volume ratio of 20:80, 30:70, 40:60, 50:50, 60:40, 70:30 and 80:20 sequentially, and the eluates obtained by eluting with chloroform-methanol at a volume ratio of (30:70), (50:50) and (80:20) were collected.

The content of the total flavone in the above extract reaches 79.0% by weight percentage, wherein the total flavone extract contains the following ingredients: 2.30% hyperin, 0.6% isoquercetin, 0.52% quercetin-3'-glucoside and 1.46% gossypetin-3'-glucoside. It was identified by LC-MS chromatography that the extract still contains quercetin, quercetin-3-robinobioside, gossypetin, myricetin and myricetin-3-glucoside.

Example 3

Preparation of the Total Flavone Extract of Flower of *Abelmoschus Manihot* (L.) *Medic*

The raw herbal material of flower of *Abelmoschus Manihot* (L.) *Medic* of the present invention is in an amount of 800 g.

Reflux extraction was performed on flower of *Abelmoschus Manihot* (L.) *Medic* by 12 times amount of 90% ethanol solution twice for 2 hours each time, and filtration was performed, then the filtrates were combined and ethanol was recovered until there was no ethanol in the filtrate, and the filtrate was concentrated to a specific gravity of 1.20, then the concentrated liquid was passed through the AB-8 macroporous adsorption resin, elution was first performed with 4 column volumes of water, then performed with 3 column volumes of 15% ethanol solution at a speed of 1 BV/h, and then performed with 3 column volumes of 70% ethanol solution at a speed of 1 BV/h, and the eluate obtained by eluting with 70% ethanol solution was collected, concentrated and dried to give a crude extract; gradient extraction was performed with the ethyl acetate-ethanol mixture at a volume ratio of 18:82, 38:62, 52:48 and 68:32 sequentially, and the extracts obtained by extracting with the ethyl acetate-ethanol mixture at a volume ratio of (18:82) and (68:32) were combined and then concentrated and dried.

The content of the total flavone in above extract reaches 82% by weight percentage, wherein the total flavone extract contains the following ingredients: 2.40% hyperin, 0.55% isoquercetin, 0.48% quercetin-3'-glucoside and 1.5% gossypetin-3'-glucoside. It was identified by LC-MS chromatography that the extract still contains quercetin, quercetin-3-robinobioside, gossypetin, myricetin and myricetin-3-glucoside.

Example 4

Capsule of the Total Flavone Extract of Flower of *Abelmoschus Manihot* (L.) *Medic*

Total flavone extract of flower of *Abelmoschus Manihot* (L.) *Medic* (prepared according to the method of Example 3) 400 g
Hydroxypropyl cellulose 20 g
Talc powder 15 g
Microcrystalline cellulose 20 g
Calcium sulfate 20 g
Anhydrous ethanol q.s.

The extract of flower of *Abelmoschus Manihot* (L.) *Medic* was pulverized, and then mixed with hydroxypropyl cellulose, talc powder, microcrystalline cellulose and calcium sulfate in above amounts, and the mixture was passed though a screen of 80 meshes, and added with an appropriate amount of anhydrous ethanol to make soft material, and then granules were prepared by a screen of 20 meshes, and dried, granulated and filled into capsules, and a total of 1000 capsules were prepared.

Example 5

Granule of the Total Flavone Extract of Flower of *Abelmoschus Manihot* (L.) *Medic*

Total flavone extract of flower of *Abelmoschus Manihot* (L.) *Medic* (prepared according to the method of Example 2) 400 g
Talc powder 15 g
Microcrystalline cellulose 20 g
Powdered sugar 10 g
3% povidone ethanol solution q.s.

The extract of flower of *Abelmoschus Manihot* (L.) *Medic* was pulverized, and then mixed with microcrystalline cellulose and powdered sugar in above amounts, and added with an appropriate amount of 3% povidone ethanol solution to make soft material, and the soft material was passed though a screen of 18 meshes, dried at 60° C. for 30~45 minutes, granulated and mixed with talc powder, then the mixture was granulated and filled into bags, a total of 1,000 bags were prepared.

Example 6

Tablet of the Total Flavone Extract of Flower of *Abelmoschus Manihot* (L.) *Medic*

Total flavone extract of flower of *Abelmoschus Manihot* (L.) *Medic* (prepared according to the method of Example 1) 400 g
Dextrin 15 g
Microcrystalline cellulose 20 g
Low-substituted hydroxypropyl methyl cellulose 20 g
Magnesium stearate 20 g
Anhydrous ethanol q.s.

The extract of flower of *Abelmoschus Manihot* (L.) *Medic*, low-substituted hydroxypropyl methyl cellulose and magnesium stearate were respectively pulverized and passed through a screen of 80 meshes, and then mixed, then the mixture was add with an appropriate amount of anhydrous ethanol solution to make soft material, then the soft material was passed through a screen of 20 meshes, and dried at 60° C. for 30~45 minutes, granulated and mixed with microcrystalline cellulose, and then the mixture was tabletted, and 1000 tablets were prepared.

Example 7

Dropping Pill of the Total Flavone Extract of Flower of Abelmoschus Manihot (L.) Medic Total Flavone Extract of Flower of Abelmoschus Manihot (L.) Medic (Prepared According to the Method of Example 3) 400 g Beeswax 40 g
Liquid paraffin 40 g
Edible vegetable oil 150 g
Gelatin 40 g
Glycerin 10 g
Water for injection q.s.

The extract of flower of Abelmoschus Manihot (L.) Medic was mixed with a melt of edible vegetable oil and beeswax (which was heated and sterilized and clarified), and stirred fully to obtain the core material. Gelatin was taken and added with an appropriate amount of water to make it expand, glycerinum and an appropriate amount of water for injection were put into the gelatin pan and heated to 70-80° C. and mixed, then the mixture was added with the expanded gelatin and stirred, melt and kept warm and let to stand for 1-2 hours, the foam at the upper layer was removed, and filtration was performed while the mixture was hot, then the filtrate was placed into the gelatin tank and kept at a temperature of 60° C., and the extract of flower of Abelmoschus Manihot (L.) Medic was slowly added into the gelatin tank; the temperature of liquid paraffin was preferably kept at 25° C., the room temperature was 15~20° C., and the temperature of dripper was 50~60° C., then the pills were dropped. The pills dropped were evenly spreaded on the gauze conveyor, and dried with a blower for 6 hours at a low temperature of 10° C. to remove the paraffin at the surface of the pills, and the pills were dried with a blower for 24 hours at a low temperature of 10° C., and dried at 45° C. for 12 hours, the waste pills were removed, and the pills were packed after passing inspection.

Example 8

Injection of the Total Flavone Extract of Flower of Abelmoschus Manihot (L.) Medic Extract of flower of Abelmoschus Manihot (L.) Medic (prepared according to the method of Example 3) 400 g
Hydroxypropyl-β-cyclodextrin 225 g
Mannitol 115 g
Water for injection q.s.

The extract of flower of Abelmoschus Manihot (L.) Medic was pulverized, and then mixed with 225 g hydroxypropyl-β-cyclodextrin, added with 5 volumes of water for injection and stirred at 60° C. for 1~2 hours, add with 115 g mannitol, and stirred to be dissolved, then the pH of the mixture was adjusted to 7.0, and the mixture was added with water for injection to make the volume of the mixture reach a total volume, and the mixture continued to be stirred for 10 minutes, then ultrafiltration was performed and the filtrate was filled into the vial and lyophilized, then the plug was pressed and the vial was sealed to obtain the injection of the extract of flower of Abelmoschus Manihot (L.) Medic.

What is claimed is:

1. A pharmaceutical composition for treating kidney disease in a subject in need thereof comprising an effective amount of a total flavone extract of flower of Abelmoschus Manihot (L.) Medic and a pharmaceutically acceptable carrier, wherein the total flavone extract of flower of Abelmoschus Manihot (L.) Medic comprises gossypetin-3'-glucoside, quercetin-3'-glucoside and isoquercetin, wherein the total flavone extract contains gossypetin-3'-glucoside, quercetin-3'-glucoside and isoquercetin in a weight ratio of 16:4:4, 14.6:5.2:6 or 15:4.8:5.5;

wherein the total flavone extract has a pharmacological activity of reducing an amount of urine protein in the subject, and wherein the pharmaceutical composition is in a form selected from the group consisting of a: capsule, tablet, pill, paste, patch, soft capsule, hard capsule and dropping pill.

2. The pharmaceutical composition according to claim 1, wherein based on the total weight of the extract, the content of total flavone in the extract by weight percentage is greater than 50%.

* * * * *